United States Patent [19]
Fujimoto et al.

[11] 3,952,100
[45] Apr. 20, 1976

[54] PHOSPHORUS NEMATOCIDES

[75] Inventors: Keimei Fujimoto, Kobe; Kunio Mukai, Amagasaki; Takaji Yamamoto, Fujisawa; Kouichi Ishibe, Kanagawa, all of Japan

[73] Assignee: Sumitomo Chemical Company, Limited, Japan

[22] Filed: July 25, 1974

[21] Appl. No.: 491,759

Related U.S. Application Data
[62] Division of Ser. No. 319,236, Dec. 29, 1972, Pat. No. 3,845,173.

[30] Foreign Application Priority Data
Dec. 30, 1971    Japan.................................. 47-1750
Dec. 30, 1971    Japan.................................. 47-1751
Jan. 8, 1972     Japan.................................. 47-4853

[52] U.S. Cl. ............................................. 424/219
[51] Int. Cl.$^2$............................................. A01N 9/36
[58] Field of Search ................................... 424/219

[56] References Cited
UNITED STATES PATENTS
3,845,173    10/1974    Fujimoto et al. ................... 260/956

FOREIGN PATENTS OR APPLICATIONS
44-29847    12/1969    Japan................................ 260/963

Primary Examiner—Frederick E. Waddell
Assistant Examiner—D. W. Robinson
Attorney, Agent, or Firm—Stewart and Kolasch, Ltd.

[57] ABSTRACT

Phosphorodithiolate compounds of the formula:

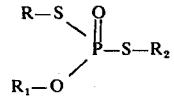

wherein $R_1$ is methyl or ethyl, $R_2$ is allyl or halogen-substituted allyl and R is n-propyl or n-butyl, provided that R is n-propyl when $R_2$ is halogen-substituted allyl and R is n-butyl when $R_2$ is allyl, which are useful as nematocides controlling a wide variety of injurious nematodes and giving little phytotoxicity to plants.

7 Claims, No Drawings

PHOSPHORUS NEMATOCIDES

This application is a divisional of copending application Ser. No. 319,236, filed on Dec. 29, 1972, now U.S. Pat. No. 3,845,173.

The present invention relates to phosphorodithiolate compounds, and their preparation and use.

Conventional nematocides include D-D (a mixture of dichloropropene and dichloropropane), EDB (ethylenedibromide), DBCP (1,2-dibromo-3-chloropropane), chloropicrin and the like. These nematocides diffuse through soil in the form of a gas to kill nematodes coming into contact with the gas. However, covering or water-sealing treatment for one or two weeks is usually necessary to complete the nematocidal activity. By the terms "covering" and "water-sealing" are meant that soil containing the gas is covered with a film such as plastic films and that the soil is filled with water through the gap therebetween, respectively. Transplanting or sowing during which the gas remains in the soil causes phytotoxicity, and therefore it is frequently necessary after such soil-treatment to leave the field as it is for a long period or to carry out the so-called "gas-removing treatment" comprising driving the gas out of the soil. Thus, sowing and setting are delayed, because the field must be left unplanted for a long period or because the tedious gas-removing treatment must be carried out. That is, phytotoxicity disturbs remarkably an effective use of the field. Moreover, chloropicrin causes the problems of pollution because of the high toxicity thereof, and commercially available nematocides mentioned above have a disadvantage that the cost per unit area is generally high.

As the result of the study on the pesticidal activity of various compounds, it has been found that a group of phosphorodithiolate compounds of the formula:

wherein $R_1$ is methyl or ethyl, $R_2$ is allyl or halogen-substituted allyl and R is n-propyl or n-butyl, provided that R is n-propyl when $R_2$ is halogen-substituted allyl and R is n-butyl when $R_2$ is allyl exhibit a strong nematocidal activity against a wide variety of nematodes including soil nematodes such as cystnematode, root-knot nematode and root lesion nematode as well as rice white-tip nematode. It has also been found that, in spite of their strong nematocidal activity, they do not show any material phytotoxicity even when applied while plants are growing. Moreover, they are very much less toxic to mammals. Thus, the said phosphorodithiolate compounds [I] are excellent nematocidal agents with a high safety, which may be applied at any time.

The phosphorodithiolate compounds [I] can easily be prepared by treating a phosphorodithioate compound of the formula:

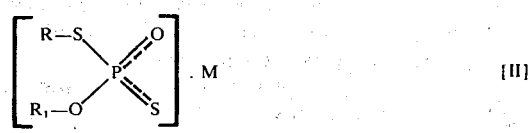

wherein M represents an alkali metal and R and $R_1$ are each as defined above with a halide of the formula:

$$R_2-Hal \qquad [III]$$

wherein Hal represents a halogen atom and $R_2$ is as defined above.

The phosphorodithiolate compounds [I] can also be prepared by treating a phosphorodithioate compound of the formula:

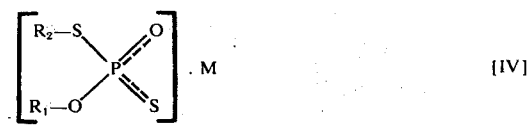

wherein $R_1$, $R_2$ and M are each as defined above with a halide of the formula:

$$R-Hal \qquad [V]$$

wherein R and Hal are each as defined above.

The phosphorodithioate compounds [II] and [IV] can be obtained by the reactions as shown in the following scheme:

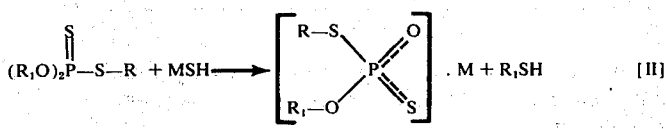

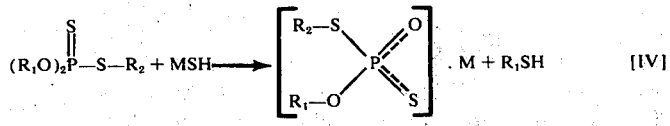

wherein R, $R_1$, $R_2$ and M are each as defined above. Specific examples of them are as follows:
Potassium O-ethyl-S-n-propylphosphorodithioate;
Sodium O-ethyl-S-n-propylphosphorodithioate;
Potassium O-methyl-S-n-propylphosphorodithioate;
Sodium O-methyl-S-n-propylphosphorodithioate;
Potassium O-ethyl-S-n-butylphosphorodithioate;
Sodium O-ethyl-S-n-butylphosphorodithioate, etc.

As the halides [III] and [V], there may be exemplified 1,3-dichloro-2-propene, 1,2-dichloro-2-propene, 1,2-dibromo-2-propene, 1,3-dibromo-2-propene, 1-chloro-2-propene, 1-bromo-2-propene, etc.

The treatment may be effected in the absence or presence of an inert solvent, usually at a temperature from room temperature to approximately 100°C or the boiling point of the inert solvent if used.

As the inert solvent, there may be preferably employed a solvent of relatively high polarity such as water, alcohols (e.g. methanol, ethanol) or ketones (e.g. acetone, methylethylketone).

The reaction time is associated with the other reaction conditions and may be ordinarily from one to several hours.

In some cases, amines or iodides may be added to the reaction system for accelerating the rate of reaction and increasing the yield.

The recovery of the phosphorodithiolate compounds [I] from the reaction mixture may be carried out by a per se conventional separation procedure.

Some typical examples of the phosphorodithiolate compounds [I] are shown in Table 1.

Table 1

| Compound No. | Chemical structure | Refractive index |
|---|---|---|
| 1 | n—C$_3$H$_7$S\\P—S—CH$_2$C=CH$_2$ / C$_2$H$_5$O, with O double bond and Br substituent | $n_D^{23.0}$ 1.5468 |
| 2 | n—C$_3$H$_7$S\\P—S—CH$_2$CH=CHCl / C$_2$H$_5$O, with O double bond | $n_D^{21.0}$ 1.5299 |
| 3 | n—C$_3$H$_7$S\\P—S—CH$_2$—C=CH$_2$ / C$_2$H$_5$O, with O double bond and Cl substituent | $n_D^{23.0}$ 1.5215 |
| 4 | n—C$_3$H$_7$S\\P—S—CH$_2$—C=CH$_2$ / CH$_3$O, with O double bond and Cl substituent | $n_D^{25.0}$ 1.5227 |
| 5 | n—C$_3$H$_7$S\\P—S—CH$_2$—CH=CHCl / CH$_3$O, with O double bond | $n_D^{22.0}$ 1.5325 |
| 6 | n—C$_3$H$_7$S\\P—S—CH$_2$—C=CH$_2$ / CH$_3$O, with O double bond and Br substituent | $n_D^{25.0}$ 1.5482 |
| 7 | n—C$_4$H$_9$S\\P—S—CH$_2$—CH=CH$_2$ / C$_2$H$_5$O, with O double bond | $n_D^{21.0}$ 1.5120 |

Some embodiments of the procedure for preparation of the phosphorodithiolate compounds [I] are shown in the following Examples.

EXAMPLE 1

To a solution of 25.1 g of potassium O-ethyl-S-n-propylphosphorodithiolate in 100 ml of ethanol, 20.0 g of 1,2-dibromo-2-propene are added, and the resultant mixture is stirred for 2 hours under reflux. After removal of the ethanol from the reaction mixture by distillation under reduced pressure, a large amount of benzene is added to the residue. The resulting solution is washed with 5 % sodium carbonate solution and then water. By removal of the benzene under reduced pressure, there are obtained 28.8 g of O-ethyl-S-n-propyl-S-(2-bromo-2-propenyl)-phosphorodithiolate (Compound No. 1) as a pale yellow oil of $n_D^{24.0}$ 1.5409.

EXAMPLE 2

As in Example 1, 25.1 g of potassium O-ethyl-S-n-propylphosphorodithioate, 11.1 g of 1,3-dichloro-2-propene and 100 ml of ethanol are treated to give 22.1 g of O-ethyl-S-n-propyl-S-(3-chloro-2-propenyl)-phosphorodithiolate (Compound No. 2) as a yellow oil of $n_D^{21.0}$ 1.5299.

EXAMPLE 3

As in Example 1, 25.1 g of potassium O-ethyl-S-n-propylphosphorodithioate, 11.1 g of 1,2-dichloro-2-propene and 100 ml of ethanol are treated to give 22.4 g of O-ethyl-S-n-propyl-S-(2-chloro-2-propenyl)-phosphorodithiolate (Compound No. 3) as a yellow oil of $n_D^{24.5}$ 1.5287.

EXAMPLES 4 TO 7

In the same manner as above, the following compounds are prepared:

O-Methyl-S-n-propyl-S-(2-chloro-2-propenyl)-phosphorodithiolate (Compound No. 4), $n_D^{25.0}$ 1.5227;

O-Methyl-S-n-propyl-S-(3-chloro-2-propenyl)-phosphorodithiolate (Compound No. 5), $n_D^{22.0}$ 1.5325;

O-Methyl-S-n-propyl-S-(2-bromo-2-propenyl)-phosphorodithiolate (Compound No. 6), $n_D^{25.0}$ 1.5482;

O-Ethyl-S-n-butyl-S-(2-propenyl)-phosphorodithiolate (Compound No. 7), $n_D^{21.0}$ 1.5120.

As stated above, the phosphorodithiolate compounds [I] possess a strong nematocidal activity with less phytotoxicity to plants. Some test results, which ensure those facts, are shown below.

TEST 1

In a pot of 1/7500 are, 900 g of soil contaminated with root-knot nematodes (Meloidgyne sp.) are placed, and a predetermined amount of an emulsifiable concentrate containing the test compound (prepared as in Example I) is applied thereto. After mixing thoroughly, six tomato young plants are transplanted (two replications). After three weeks, the growth and the degree of root-knot on which root-knot nematodes are parasitic as well as the phytotoxicity are observed.

The results are shown in Table 2 wherein the values of the plant height and the root weight are the averages, and the degree of root-knot and the phytotoxicity are classified into the following five grades:

Root-knot:

| Degree of root-knot | 0 | 1 | 2 | 3 | 4 |
|---|---|---|---|---|---|
| Degree of parasitism | None | Low | Medium | High | Very high |

Phytotoxicity:

—, phytotoxicity is not recognized;

±, plant is a little bad in growth, and leaf partially changes color;

+, plant is bad in growth, and leaf partially changes brown;

++, plant is very bad in growth, very small, and leaf wholly changes brown;

+++, plant is almost dead.

Table 2

| Compound No. | Active ingredient (kg/10a.) | Growth Plant height (cm) | Growth Root weight (g/plant) | Degree of root-knot | Phytotoxicity |
|---|---|---|---|---|---|
| 1 | 0.38 | 17.8 | 0.62 | 0 | — |
|   | 0.75 | 17.5 | 0.60 | 0 | — |
|   | 1.5  | 17.4 | 0.58 | 0 | — |
|   | 3.0  | 16.5 | 0.53 | 0 | — |
| 2 | 0.38 | 17.6 | 0.64 | 0 | — |
|   | 0.75 | 17.4 | 0.61 | 0 | — |
|   | 1.5  | 17.1 | 0.59 | 0 | — |
|   | 3.0  | 16.3 | 0.51 | 0 | — |
| 3 | 0.38 | 18.1 | 0.64 | 0 | — |
|   | 0.75 | 18.0 | 0.63 | 0 | — |
|   | 1.5  | 17.9 | 0.62 | 0 | — |
|   | 3.0  | 17.7 | 0.59 | 0 | — |
| 4 | 0.38 | 17.2 | 0.67 | 0 | — |
|   | 0.75 | 17.0 | 0.63 | 0 | — |
|   | 1.5  | 17.1 | 0.66 | 0 | — |
|   | 3.0  | 16.3 | 0.59 | 0 | — |
| 5 | 0.38 | 17.9 | 0.68 | 0 | — |
|   | 0.75 | 17.5 | 0.66 | 0 | — |

Table 2-continued

| Compound No. | Active ingredient (kg/10a) | Plant height (cm) | Root weight (g/plant) | Degree of root-knot | Phytotoxicity |
|---|---|---|---|---|---|
|   | 1.5 | 17.8 | 0.67 | 0 | — |
|   | 3.0 | 16.9 | 0.58 | 0 | — |
|   | 0.38 | 18.0 | 0.62 | 0 | — |
| 6 | 0.75 | 17.7 | 0.59 | 0 | — |
|   | 1.5 | 17.9 | 0.57 | 0 | — |
|   | 3.0 | 17.1 | 0.51 | 0 | — |
|   | 0.38 | 18.2 | 0.69 | 0 | — |
| 7 | 0.75 | 18.0 | 0.65 | 0 | — |
|   | 1.5 | 18.2 | 0.68 | 0 | — |
|   | 3.0 | 17.5 | 0.61 | 0 | — |
| Standard DBCP | 3.0 | 14.6 | 0.51 | 0.7 | + |
| Standard D-D | 1.5 | — | — | — | +++ |
| No treatment | — | 15.0 | 0.45 | 3.5 | — |

TEST 2

After application of the test compound as in Test 1, 10 seeds of tomato are sowed, and the growth, the degree of root-knot and the phytotoxicity are observed three weeks thereafter.

The results are shown in Table 3 wherein the criteria are as in Test 1.

Table 3

| Compound No. | Active ingredient (kg/10a) | Plant height (cm) | Root weight (g/plant) | Degree of root-knot | Phytotoxicity |
|---|---|---|---|---|---|
| 1 | 0.38 | 11.2 | 0.17 | 0.2 | — |
|   | 0.75 | 11.8 | 0.16 | 0 | — |
|   | 1.5 | 11.5 | 0.15 | 0 | — |
|   | 3.0 | 11.7 | 0.17 | 0 | — |
| 2 | 0.38 | 11.1 | 0.18 | 0.1 | — |
|   | 0.75 | 12.4 | 0.22 | 0 | — |
|   | 1.5 | 12.4 | 0.24 | 0 | — |
|   | 3.0 | 12.3 | 0.16 | 0 | — |
| 3 | 0.38 | 14.1 | 0.10 | 0 | — |
|   | 0.75 | 10.8 | 0.13 | 0 | — |
|   | 1.5 | 10.1 | 0.09 | 0.1 | ± |
|   | 3.0 | 9.7 | 0.08 | 0.1 | ± |
| 4 | 0.38 | 10.4 | 0.12 | 0.4 | — |
|   | 0.75 | 11.2 | 0.12 | 0 | — |
|   | 1.5 | 10.7 | 0.14 | 0 | — |
|   | 3.0 | 10.1 | 0.12 | 0 | — |
| 5 | 0.38 | 11.0 | 0.15 | 0.1 | — |
|   | 0.75 | 11.1 | 0.16 | 0 | — |
|   | 1.5 | 10.7 | 0.15 | 0 | — |
|   | 3.0 | 10.3 | 0.12 | 0 | — |
| 6 | 0.38 | 11.2 | 0.18 | 0 | — |
|   | 0.75 | 10.9 | 0.17 | 0 | — |
|   | 1.5 | 11.0 | 0.13 | 0 | — |
|   | 3.0 | 10.7 | 0.10 | 0 | — |
| 7 | 0.38 | 11.5 | 0.16 | 0.2 | — |
|   | 0.75 | 11.3 | 0.14 | 0 | — |
|   | 1.5 | 11.5 | 0.14 | 0 | — |
|   | 3.0 | 10.8 | 0.13 | 0 | — |
| Standard DBCP | 3.0 | 10.5 | 0.10 | 0.3 | ± |
| Standard D-D | 1.5 | — | — | — | No germination |
| No treatment | — | 9.4 | 0.08 | 3.5 | — |

TEST 3

In vats of 40 cm × 30 cm, there are transplanted kidney bean (2 leaves stage), cucumber (3 leaves stage), tomato (4 leaves stage), carrot (2 leaves stage), beet (4 leaves stage), tobacco (3 leaves stage) and lettuce (4 leaves stage). Seven days after the transplantation, a predetermined concentration of the test compound in solution is applied at a rate of 3 liters per m$^2$, and the vats are kept in a greenhouse. Phytotoxicity is observed 20 days after the application. Tests are carried out in two replications, i.e. a and b.

The results are shown in Table 4 wherein the criteria are as in Test 1.

Table 4

| Compound No. | Concentration (ppm) | Kidney bean | | Cucumber | | Tomato | | Carrot | | Beet | | Tobacco | | Lettuce | |
|---|---|---|---|---|---|---|---|---|---|---|---|---|---|---|---|
|   |   | a | b | a | b | a | b | a | b | a | b | a | b | a | b |
| 1 | 1000 | — | — | — | — | — | — | — | — | — | — | — | — | — | — |
| 2 | 1000 | — | — | — | — | — | — | — | — | — | — | — | — | — | — |
| 3 | 1000 | — | — | — | — | — | — | — | — | — | — | — | — | — | — |
| 4 | 1000 | — | — | — | — | — | — | — | — | — | — | — | — | — | — |
| 5 | 1000 | — | — | — | — | — | — | — | — | — | — | — | — | — | — |
| 6 | 1000 | — | — | — | — | — | — | — | — | — | — | — | — | — | — |
| 7 | 1000 | — | — | — | — | — | — | — | — | — | — | — | — | — | — |
| Standard DBCP | 1000 | — | — | — | — | + | + | — | — | — | — | ++ | ++ | ++ | ++ |
| No treatment | — | — | — | — | — | — | — | — | — | — | — | — | — | — | — |

In addition to the nematocidal activity, the phosphorodithiolate compounds [I] exhibit insecticidal and acaricidal activities. Since their acute and chronic toxicities to warm blooded-animals are low, they are practically utilizable as pesticides, particularly as nematocides.

Most of the phosphorodithiolate compounds [I] are liquid and can be applied as such or together with any liquid or solid carrier, or in some cases, in a gaseous form. Alternatively, they can be applied in conventional manners as emulsifiable concentrates, wettable powders, oil sprays, dusts, ointments, granules, fine granules, aerosols or fumigants formulated by any conventional method, if necessary, including any auxiliary chemical. They can also be applied, needless to say, in the form of mixtures with other nematocides, insecticides, herbicides, fungicides, seed disinfectants, fertilizers or soil disinfectants.

Some embodiments of the composition containing the phosphorodithiolate compound [I] as an active ingredient are illustratively shown in the following Examples wherein parts are by weight.

EXAMPLE I

O-Ethyl-S-n-propyl-S-(2-bromo-2-propenyl)-phosphorodithiolate (50 parts), an emulsifier (tradename "Sorpol 3002") (20 parts) and xylene (30 parts) are mixed thoroughly to make an emulsifiable concentrate.

EXAMPLE II

O-Ethyl-S-n-propyl-S-(3-chloro-2-propenyl)-phosphorodithiolate (25 parts), white carbon (13 parts), lauryl sulfate (5 parts), calcium ligninsulfonate (5 parts) and clay (52 parts) are mixed and pulverized thoroughly to make a wettable powder.

EXAMPLE III

O-Ethyl-S-n-propyl-S-(2-chloro-2-propenyl)-phosphorodithiolate (5 parts) and clay (95 parts) are mixed and pulverized to make a dust.

What is claimed is:

1. A nematocidal composition containing, as an active ingredient, a nematocidally effective amount of a phosphorodithiolate compound of the formula:

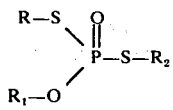

wherein $R_1$ is methyl or ethyl, $R_2$ is chlorine- or bromine-substituted allyl, and R is n-propyl, and a conventional inert carrier.

2. The nematocidal composition of claim 1, wherein said composition is in the form of an emulsifiable concentrate, a wettable powder or a dust.

3. The nematocidal composition of claim 1, wherein the phosphorodithiolate compound has the formula:

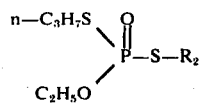

wherein $R_2$ is chlorine or bromine-substituted allyl.

4. The nematocidal composition of claim 1, wherein said phosphorodithiolate compound has the formula:

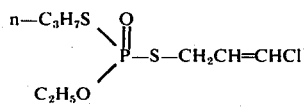

5. The nematocidal composition of claim 1, wherein said phosphorodithiolate compound has the formula:

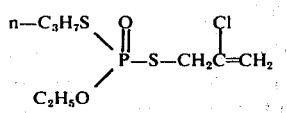

6. The nematocidal composition of claim 1, wherein the phosphorodithiolate compound has the formula:

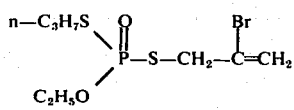

7. A method for combatting nematodes which comprises applying to a nematode a nematocidally effective amount of the phosphorodithiolate compound of claim 1.

* * * * *